(12) United States Patent
Mosler et al.

(10) Patent No.: US 8,906,113 B2
(45) Date of Patent: Dec. 9, 2014

(54) PROSTHESIS

(71) Applicant: Otto Bock HealthCare GmbH, Duderstadt (DE)

(72) Inventors: Lueder Mosler, Duderstadt (DE); Scott Weber, St. Cloud, MN (US)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

(21) Appl. No.: 13/685,200

(22) Filed: Nov. 26, 2012

(65) Prior Publication Data

US 2013/0150982 A1  Jun. 13, 2013

(30) Foreign Application Priority Data

Nov. 29, 2011 (DE) .......................... 10 2011 119 591

(51) Int. Cl.
*A61F 2/80* (2006.01)
*A61F 2/60* (2006.01)
*A61F 2/78* (2006.01)
*F04B 43/08* (2006.01)
*F04B 43/12* (2006.01)
*F04B 45/06* (2006.01)
*A61F 2/48* (2006.01)

(52) U.S. Cl.
CPC ............. *A61F 2/80* (2013.01); *A61F 2002/802* (2013.01)

USPC ................... 623/34; 623/36; 623/33; 623/24; 417/476; 417/474

(58) Field of Classification Search
USPC .............................................. 623/34; 417/476
See application file for complete search history.

(56) References Cited

U.S. PATENT DOCUMENTS

| 2,899,905 | A | * | 8/1959 | Beacher ........................ 417/475 |
| 5,904,722 | A | * | 5/1999 | Caspers ........................... 623/34 |
| 2003/0181990 | A1 | | 9/2003 | Phillips | |
| 2006/0212128 | A1 | | 9/2006 | Nachbar | |
| 2006/0224247 | A1 | * | 10/2006 | Clausen et al. ................. 623/24 |
| 2011/0184532 | A1 | | 7/2011 | Tompkins | |

FOREIGN PATENT DOCUMENTS

WO  2006/135851  12/2006

* cited by examiner

*Primary Examiner* — David Isabella
*Assistant Examiner* — Jacqueline Woznicki
(74) *Attorney, Agent, or Firm* — Whitham Curtis Christofferson & Cook, PC

(57) ABSTRACT

The invention relates to a prosthesis with a prosthesis socket which has an inner face and is designed to be arranged on an amputation stump after a liner has been pulled over the latter, such that the inner face is directed toward the liner and a volume is enclosed between the inner face and the liner, and with a pump for generating an underpressure in the volume when the prosthesis socket is arranged on the amputation stump, characterized in that the pump is a peristaltic pump (1).

16 Claims, 12 Drawing Sheets

PROSTHESIS

FIELD OF THE INVENTION

The invention relates to a prosthesis with a prosthesis socket which has an inner face and is designed to be arranged on an amputation stump, such that the inner face is directed toward the amputation stump and a volume is enclosed between the inner face and the amputation stump, and with a pump for generating an underpressure in the volume when the prosthesis socket is arranged on the amputation stump.

BACKGROUND

Today, prostheses of this kind are well known from the prior art. A liner is often first pulled over the amputation stump. This liner can be made of a silicone material or a polyurethane material, for example, which has been adapted to the individual shape of the particular amputation stump. The prosthesis socket of the prosthesis is then pulled over this liner such that the inner face of the prosthesis socket is directed toward the liner and therefore toward the amputation stump. If no separate liner is used, the inner face of the prosthesis socket directly faces the amputation stump. Alternatively, a sleeve, for example, can also be pulled over the amputation stump and provides an airtight seal between the upper edge, i.e. proximal edge, of the prosthesis socket and the amputation stump. In order to fix the prosthesis socket and therefore the prosthesis at the desired place, and to ensure this even when the patient performs considerable movements for example, it is known from the prior art to generate an underpressure between the liner and the prosthesis socket, by means of which underpressure the prosthesis socket is held in its position. Arrangements of very different kinds are known for this purpose.

Generally, the prosthesis socket has a distal through-opening to which a vacuum pump is attached. An arrangement of this kind is known from WO 2006/135851 A2, for example. The vacuum pump, together with a power source provided therefore, is part of the prosthesis set-up. If such a prosthesis is worn over a fairly long period, for example for one day, it is possible for air to penetrate into the volume between the liner and the inner face of the prosthesis socket on account of the movement of the amputation stump and of the prosthesis socket and because of small leaks. The underpressure is thereby reduced, as a result of which the fastening of the prosthesis to the amputation stump is weakened.

For this eventuality, the person wearing a prosthesis described in WO 2006/135851 A2 always has on him the vacuum pump as part of the prosthesis, and therefore, if the underpressure drops, he is able to reactivate the pump and adjust the underpressure to the desired strength.

A disadvantage is that a pump of this kind, which is often designed as a diaphragm pump, is heavy and takes up a lot of space, and it cannot therefore be accommodated in every prosthesis. Moreover, a sufficient power supply has to be provided, for example in the form of batteries. In addition, diaphragm pumps have to be supplemented by valves which, if they become dirty, can impair the reliable function of the pump. To be able to use a diaphragm pump both as a vacuum pump and also as a release pump, elaborate valve circuitry is also necessary.

To overcome this disadvantage, it is known, for example from U.S. Pat. Nos. 5,702,489 and 6,926,742, to provide an external vacuum pump. The disadvantage of this system, however, is that the person wearing the prosthesis always has to carry the pump around as a separate component, so as to be able to attach the pump in the event of a possible pressure loss between the liner and the prosthesis socket. Moreover, he then has to attach the vacuum pump to a corresponding device, which can be provided on the prosthesis socket for example, which proves difficult, if not impossible, particularly for elderly persons or persons of reduced mobility who wear prosthesis systems.

Regardless of whether an external or an internal vacuum pump is provided for a prosthesis, these systems all have a valve system which, once the underpressure has been set, ensure that air cannot penetrate into the volume between the liner and the prosthesis socket. Valves of this kind comprise movable parts and are thus susceptible to becoming dirty and malfunctioning and, accordingly, they require considerable maintenance. In addition, production is relatively complicated and expensive. Another factor is that valves may also be accidentally or incorrectly operated by the person wearing the prosthesis, with the result that air can penetrate into the volume between the liner and the prosthesis socket. In this case, a secure fit of the prosthesis on the amputation stump can no longer be ensured.

SUMMARY

The problem addressed by the invention is therefore to develop a prosthesis of the type in question in such a way as to greatly reduce the number of parts that are movable and thus susceptible to malfunction, virtually eliminating the possibility of incorrect operation, and yet provide a space-saving, energy-saving and cost-effective solution to the provision of the necessary underpressure.

The invention solves the stated problem by providing a prosthesis of the type in question in which the pump for generating the underpressure within the volume is a peristaltic pump. It is immaterial to the invention whether the prosthesis socket of the prosthesis according to the invention, bears directly on the amputation stump of the patient or whether an intermediate layer, for example a liner, or another kind of closure of the volume is provided. It is important simply that an airtight volume is defined in which an underpressure can be produced, by means of which the prosthesis is held on the amputation stump. It is also immaterial how large this volume is, i.e. how far the airtight closure is in the proximal direction from the suction point of the pump.

The pumping principle of a peristaltic pump is that a medium, in the present case air from the volume between the amputation stump, or a liner pulled over the latter, and the prosthesis socket, is forced through a hose by the mechanical deformation of the hose.

In a particularly preferred embodiment, the peristaltic pump comprises a housing which has a circumferential wall, a floor and a lid. Inside this housing, a hose is guided along the inner side of the circumferential wall. The peristaltic pump has at least one pump element, in a preferred illustrative embodiment exactly one pump element. The latter is mounted, for example, on a shaft that extends centrally in the housing in the axial direction, i.e. from the floor to the lid of the housing. The at least one, preferably exactly one, pump element rotates about the shaft and, at its radially outer side, squeezes shut the hose extending between it and the inner side of the circumferential wall of the housing. By means of the continued movement of the pump element in the circumferential direction, the conveyed medium enclosed in the hose is pressed forward through the hose. It is of course also possible for two or more pump elements to be present.

Peristaltic pumps have long been known from the prior art. Their advantages include the gentle transport of sensitive material to be conveyed, for example blood cells, which would be destroyed for example by rapidly rotating propeller blades of other pumping technologies. Therefore, peristaltic pumps, which are also called hose pumps, are used particularly in infusion pumps and as blood pumps in dialysis appliances and heart-lung machines. They are always used when a sensitive material has to be uniformly pumped over a long period of time. Consequently, they were hitherto considered unsuitable for the purpose concerned here.

There are several reasons for this. First, permanent operation is not needed in the use of a peristaltic pump as described here. Instead, the underpressure in the volume between the prosthesis socket and the liner is produced when the prosthesis is fitted in place. As soon as the underpressure has been set, the pump is switched off and, in the optimal scenario, is also not used again. In addition, peristaltic pumps function best when the pressure in the hose is equal to or slightly greater than the pressure inside the housing, but outside the hose, since the hose has to return to its original shape, after it has been squeezed shut by the at least one pump element, in order to be available to receive further material to be conveyed. It was therefore assumed that an underpressure at which the pressure inside the hose is much lower than the pressure outside the hose but inside the housing of the pump cannot be produced using a pump of this kind. Surprisingly, this was found to be incorrect.

For the production of an underpressure, it is expedient that the pump generates the greatest possible stroke, i.e. uses the fewest possible pump elements. Therefore, in a particularly preferred embodiment, the peristaltic pump comprises exactly one pump element. Preferably, the circumferential wall of the housing of the peristaltic pump has an opening through which the hose is guided into the housing and out of the housing. The hose is particularly advantageously guided in such a way that at no point does the hose overlap itself. For example, it is expedient to insert the hose through the opening into the housing of the peristaltic pump, guide it once along the inner side of the circumferential wall and out again through the same opening through which it was inserted into the housing. The hose thus runs in a very sharp bend directly after entering the housing and directly before leaving the housing, so as to avoid the hose overlapping itself. A "kink" of this kind in the run of the hose is preferable to an overlapping, since such overlapping would not only lead to a larger overall structure but also to a much increased radial force on the at least one pump element in this area. The bend can be made less sharp if the hose is guided into and out of the pump housing through an oval opening.

The pump element has to press the hose together at the narrowest point between the one pump element and the inner side of the circumferential wall. However, if there are one or more locations where the hose is doubled, i.e. where the hose overlaps itself, the pump element has to squeeze the hose shut twice at this location. This results in a greatly increased force, which is transferred to the centrally running shaft. The described embodiment is advantageous for keeping this force as low as possible. However, even in this embodiment, in order to be able to ensure a perfect function of the pump, the pump element has to press shut both the hose end entering the housing and also the hose end leaving the housing, so as to prevent more air from flowing into the already pumped vacuum or the already pumped underpressure. For this reason, it is particularly advantageous for the hose ends to be guided into and out of the housing directly next to each other through one opening.

It has likewise proven advantageous if the pump element is a roller, which is arranged in the housing such that it can rotate about the shaft and pinches the hose shut. The hose is advantageously guided along the inner side of the circumferential wall and forms a frictional planetary gear together with the roller and the shaft. In this case, in order to apply the necessary torque, it is not necessary to arrange a separate gear mechanism between the pump head, i.e. the actual pump, and a motor used to drive the pump. This gear mechanism is provided by the described frictional planetary gear composed of shaft, roller and hose. The roller, i.e. the at least one pump element, is inserted with prestressing between the shaft, which extends from the floor to the lid of the housing, and the hose. This prestressing results in a frictional contact between the roller and the shaft, by which means the transfer of the torque is permitted. By way of the diameter ratio of shaft and roller, it is possible to change the transmission ratio and adapt it to the particular embodiment desired. If the shaft is now set in motion via the rotary movement of the motor, the torque is transferred to the roller by the frictional contact, and the roller thus moves along the hose about the shaft.

For this purpose, it is particularly advantageous if the at least one pump element, i.e. the roller, and the shaft are coated with a material that increases friction, for example a plastic. Alternatively, for example, the motor shaft or another component can also be made from stainless steel, in which case the surface is roughened, for example by a laser erosion technique, at least at the locations where the shaft comes into contact with the roller.

The roller is advantageously designed in the form of a hollow roller. The use of a hollow roller ensures that the peristaltic pump, and therefore the prosthesis, can be used within a greater temperature range. For example, it is possible to compensate for the thermal expansions of the roller within a temperature range of $-20°$ C. to $+60°$ C. Particularly when using a frictional planetary gear, as has been described above, certain tolerances in respect of the individual diameters of the components used are necessary. If the at least one roller were designed in the form of a solid roller, this would lead to the gear slipping at low temperatures for example, such that the necessary torque would no longer be transferred and the functionality of the peristaltic pump would be limited. At high temperatures, the expansion of the roller would lead to increased bending moments on the shaft and therefore on the motor bearing.

To further reduce the energy requirements of the peristaltic pump, a friction-reducing layer, for example a PTFE fabric sheet, is preferably applied to an inner side of the lid and/or to an inner side of the floor of the housing. It is generally advantageous if the movable components, in particular the shaft and the at least one roller, are mounted with the least possible friction. For example, it is expedient to mount the shaft at both ends in a ball bearing in order to minimize friction losses.

The hose is advantageously made of silicone or of a thermoplastic elastomer or of polyurethane. The thermoplastic elastomer is preferred since it has a much lower air permeability than silicone. As a result, less air penetrates right through the hose, which is particularly advantageous when the peristaltic pump is switched off, since the necessary underpressure in the volume between the liner and the prosthesis socket has already been produced. Alternatively, other materials are also conceivable. For example, the hose can also be made of a natural rubber or TPE.

If, after the prosthesis has been put on, the necessary underpressure has already been produced by the peristaltic pump, the pump can simply be switched off. Even in this state, the at least one pump element presses the hose safely shut, such that entry of air into the volume in which the underpressure has been produced is safely avoided without having to provide separate valves or valve systems fitted with movable parts. Not only does this reduce the production outlay and therefore the production costs, it also means that less installation space is needed, such that the pump arrangement with the peristaltic pump can also be used in smaller prostheses.

To further enhance this effect, a disk rotor motor can be used as the motor for driving the pump. These motors are basically electric motors in which the rotors have the shape of a disk. They can, in particular also be designed without a separate iron core, as a result of which they can be made very light and therefore, have a low moment of inertia. They can, therefore, accelerate or brake particularly quickly. Moreover, magnetic forces act on the rotor only when current passes through the disk. For the purpose of use that is intended here, the greatest advantage of a disk rotor motor of this kind is, in addition to its low weight, the fact that it can run very smoothly and quietly even at low speeds. It is thus also possible to do without a step-down gear mechanism, as a result of which the number of movable parts is further reduced and the production and assembly costs are likewise further reduced. In addition, the required installation space is further reduced. The usual speeds are, for example, 300 revolutions per minute or preferably less, for example 150 to 250 revolutions per minute.

In a preferred embodiment, the inner side of the circumferential wall of the housing of the pump is provided with an inner contour, the effect of which is that the hose mounted therein cannot slip in the axial direction and is instead held in this position. In the choice of the hose parameters, particular care should be taken to ensure that the hose opens up again after it has been squeezed shut by the one pump element, i.e. the roller, even in view of the large pressure difference between its interior and the housing. Examples of suitable Shore hardness values for the hose are from 60 to 65, if the hose has an external diameter of 5 mm, for example, and a wall thickness of 1 mm. Of course, combinations of greater hardness and smaller wall thickness are also conceivable. With a peristaltic pump of this kind, it is possible to achieve underpressures of as much as 900 mbar in the volume between the liner and the prosthesis socket. If the hose is made of a thermoplastic elastomer for example, it has a very high degree of resistance to wear, which is advantageous for the use in a peristaltic pump. During pumping, the hose is subjected to a constant flexing stress in the form of a mechanical alternating load. In addition, the material has a high recovery capacity, such that the hose can be prevented from collapsing even with substantial underpressures.

It has proven advantageous for the hose to have a cross section which ensures that, when the hose is pressed shut by being squeezed between the one pump element and the inside wall of the housing, no bead formation whatsoever or only very slight bead formation can be observed. This can be achieved, for example, if the hose has a smaller wall thickness at two opposite locations in the cross section. Alternatively or in addition to this, cross sections that deviate from a circular cross section are also conceivable.

To ensure that the hose can easily open up again after it has been pressed shut by the pump element, a vacuum can be provided in the interior of the housing, as a result of which the pressure difference between the interior of the housing and the interior of the hose is reduced.

In addition to or as an alternative to this, the hose can in particular be coated on the inside, but also on the outside, for example by means of CVD (chemical vapor deposition), such that possible adherence of the inner walls of the hose to each other can be at least reduced or completely avoided.

BRIEF DESCRIPTION OF THE DRAWINGS

An illustrative embodiment of the present invention is explained in more detail below with reference to a drawing, in which.

DETAILED DESCRIPTION

Figure 1:
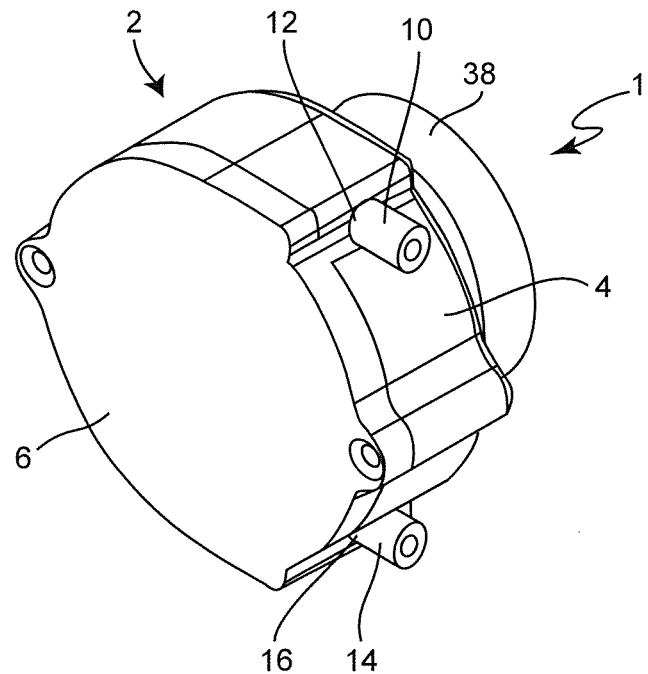
FIG. 1 shows the schematic view of a peristaltic pump for a prosthesis according to a first illustrative embodiment of the present invention.

FIG. 1 shows a peristaltic pump 1, which has a housing 2 with a circumferential wall 4, a lid 6 and a floor 8 (not shown). FIG. 1 shows a first hose end 10, which is guided into the housing 2 through a first opening 12 located in the circumferential wall 4 of the housing 2. A second hose end 14 is guided out of the housing 2 through a second opening 16. A motor 38 is arranged on the floor 8.

Figure 2:
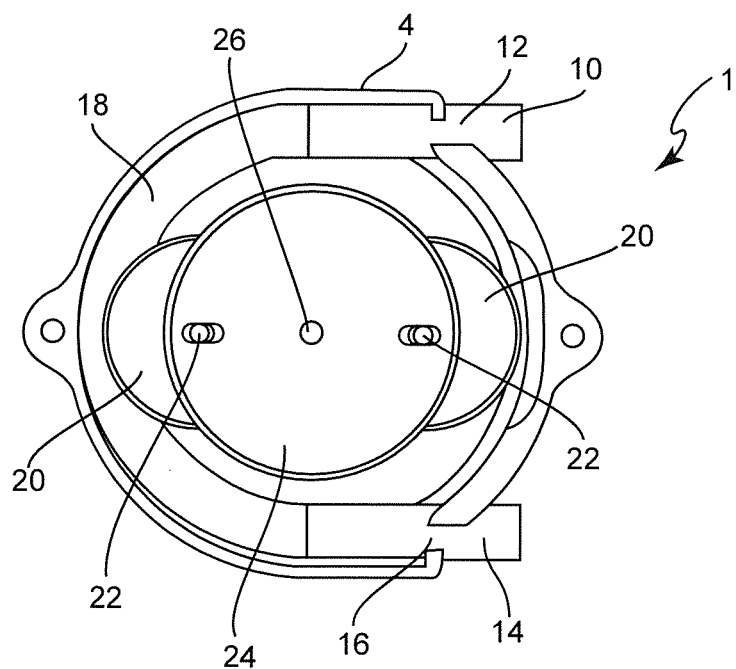
FIG. 2 shows the pump from FIG. 1 in a schematic plan view.

FIG. 2 shows a schematic plan view of an opened peristaltic pump 1 according to FIG. 1. This view shows the circumferential wall 4 and also the first hose end 10 and second hose end 14 that are guided through a first opening 12 and a second opening 16, respectively, in the circumferential wall 4. In the housing 2 itself, a hose 18 extends along the circumferential wall 4. In the embodiment shown in FIG. 2, the peristaltic pump 1 has two pump elements 20. The two pump elements 20 are designed in the form of rollers. These are mounted rotatably about a respective roller axle 22. In the illustrative embodiment shown in FIG. 2, the roller axles 22 extend perpendicularly with respect to the plane of the drawing. They are mounted in a spacing disk 24 having a shaft 26 via which they can be moved in rotation by means of a motor (not shown). It will be seen from the left-hand side of FIG. 2 that the pump element 20 shown on the left squeezes the hose 18 between itself and the circumferential wall 4. If the shaft 26 is now moved in rotation, for example clockwise, the two pump elements 20 move counterclockwise. In doing so, the left-hand pump element 20 in FIG. 2 pushes a medium located in the hose 18 in the direction of the second hose end 14. Before the left-hand pump element 20 in FIG. 2 frees the hose 18 again, the right-hand pump element 20 in FIG. 2 presses the hose 18 shut again near the first opening 12, such that a return flow of the medium through the first hose end 18 is impossible. The spacing disk 24 ensures that both pump elements 20 are always arranged opposite each other. The elongate holes that are provided can compensate for tolerances and, for example, the thermal expansion.

Figure 3:
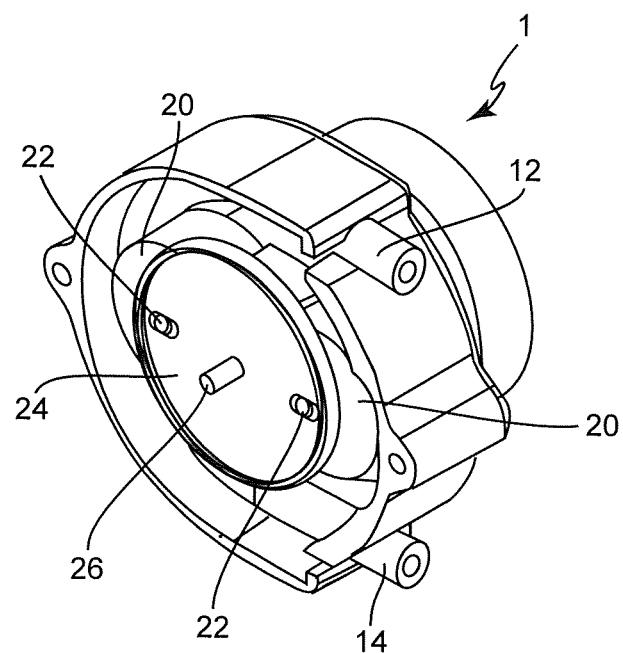
FIG. 3 shows another view of a peristaltic pump.

FIG. 3 shows the view from FIG. 2 at another angle.

Figure 4:
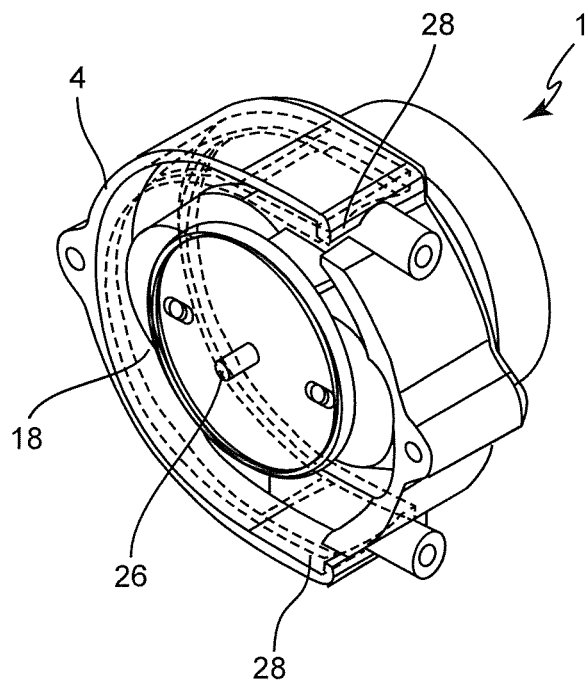
FIG. 4 shows another view of a peristaltic pump.

FIG. 4 shows the peristaltic pump 1 shown in FIGS. 2 and 3, a guide 28 now being arranged on the inside face of the circumferential wall 4, which guide 28 can be made from a silicone for example. It is designed in the form of a peripheral groove in which the hose 18 is arranged. This prevents slipping or shifting of the hose 18 in the axial direction relative to the shaft 26. In addition, manufacturing tolerances and the thermal expansion of the individual components are compensated.

Figure 5:
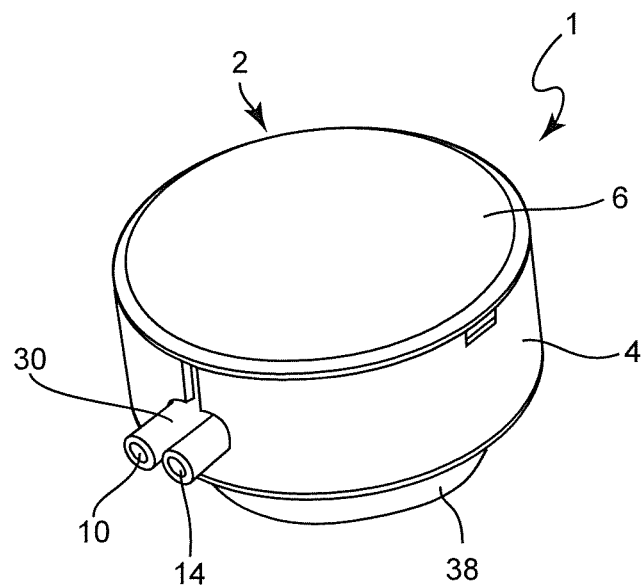
FIG. 5 shows a schematic 3D view of a peristaltic pump for a prosthesis according to another illustrative embodiment of the present invention.

FIG. 5 shows a schematic 3D view of a peristaltic pump 1 for a prosthesis according to another illustrative embodiment of the present invention. This peristaltic pump also has a housing 2 with the circumferential wall 4, the lid 6, and the floor 8 on which the motor 38 is arranged. It will be noted, however, that the circumferential wall 4 is provided with only one opening 30, through which both the first hose end 10 and also the second hose end 14 are guided.

Figure 6:
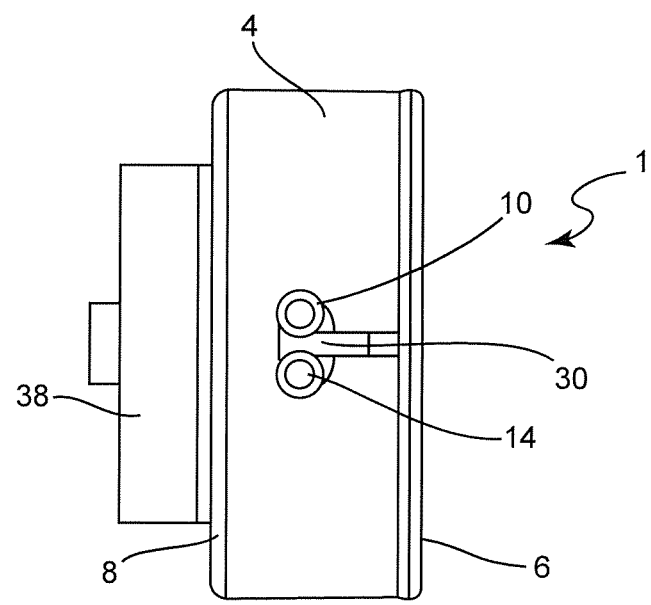
FIG. 6 shows the pump from FIG. 5 in a schematic side view.

FIG. 6 shows the illustration from FIG. 5 in a side view. It shows the first hose end 10 and the second hose end 14, which are guided directly next to each other through the opening 30. Although a small space is shown in FIG. 6 between the first hose end 10 and the second hose end 14, it is also possible, and particularly advantageous, for both hose ends 10, 14 to be guided out of the opening 30 directly next to each other, i.e. touching each other.

Figure 7:
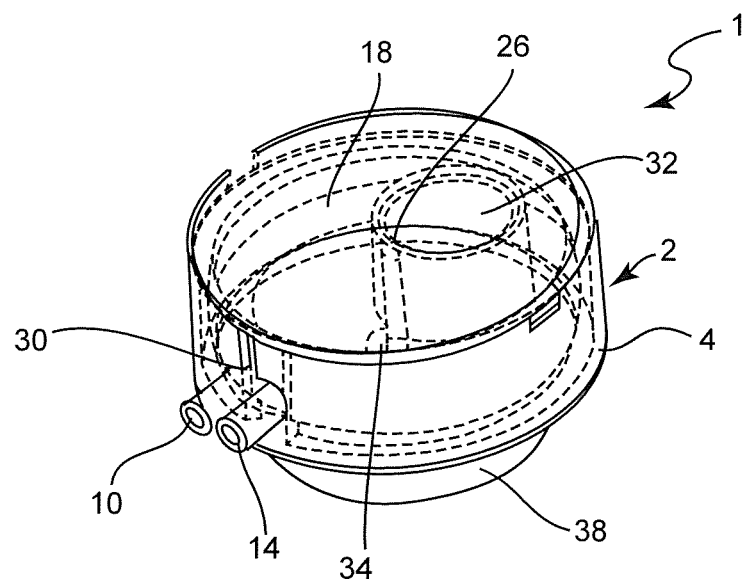
FIG. 7 shows a schematic view of an opened peristaltic pump.

FIG. 7 shows the view of an opened peristaltic pump according to FIGS. 5 and 6, the lid 6 having been removed. The first hose end 10 passes through the opening 30 into the housing 2 of the peristaltic pump 1. In the illustrative embodiment shown in FIG. 7, the hose 18 makes a curve to the left and is guided once along the inside face of the circumferential wall 4. As soon as the hose 18 reaches the opening 30 again, the second hose end 14 is guided out through the opening 30.

The interior of the housing 2 contains a shaft 26 and a roller 32, which represents the only pump element of the peristaltic pump 1 shown in FIG. 7. The roller 32 is designed as a hollow roller, in order to take account of the expansion and/or contraction in the event of temperature variations. The shaft 26 has a roughened area 34, which is exactly the area in which the shaft 26 comes into contact with the roller 32. Alternatively or in addition, the shaft 26 can also be grooved or toothed or provided with another structure by which the friction between shaft 26 and roller 32 is increased. The circumferential surface of the roller 32 can likewise be roughened or coated with a material that increases friction. It will be noted that, unlike the situation in FIGS. 2, 3 and 4, the roller 32 does not have a roller axle. Instead, the necessary torque from the shaft 26, which can be driven by a motor (not shown), is transferred to the roller 32 exclusively by the frictional contact between the shaft 26 and the roller 32. The roller 32 pinches the hose 18 between itself and the inside face of the circumferential wall 4 and thus presses the hose 18 shut. The shaft 26, the roller 32 and the hose 18 thus form a frictional planetary gear. By this means, noise development is also greatly reduced and the pump 1 runs almost silently.

Figure 8:
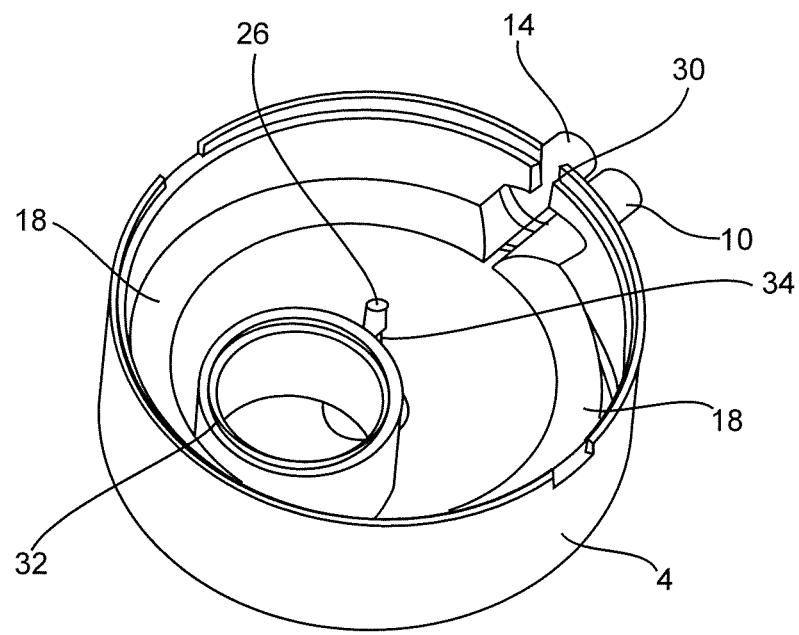
FIG. 8 shows another schematic view of an opened peristaltic pump.

FIG. 8 shows a simplified view from a slightly different angle. The first hose end 10 is guided through the opening 30. In the interior of the housing 2, the hose in FIG. 8 makes a curve to the left and is guided along the inside face of the circumferential wall 4. After it has again reached the opening 30, the second hose end 14 is guided out through the opening 30. The view in FIG. 8 clearly shows that, in this embodiment, the hose 18 does not overlap itself. It instead forms a flat loop, which ensures that the hose 18 is guided exactly once along the inside face of the circumferential wall 4 around the shaft 26, without having to be guided over itself particularly in the area of the opening 30. In order also to ensure, in this embodiment, that no air can flow back through the hose 18 into the already evacuated volume, the roller 32, in the area of the opening 30, has to press the hose 18 shut both in the area of the first hose end 10 and also in the area of the second hose end 14. It is therefore advantageous if both hose ends 10, 14 are guided as closely adjacent to each other as possible into the housing 2 and out of the housing 2.

Figure 9:
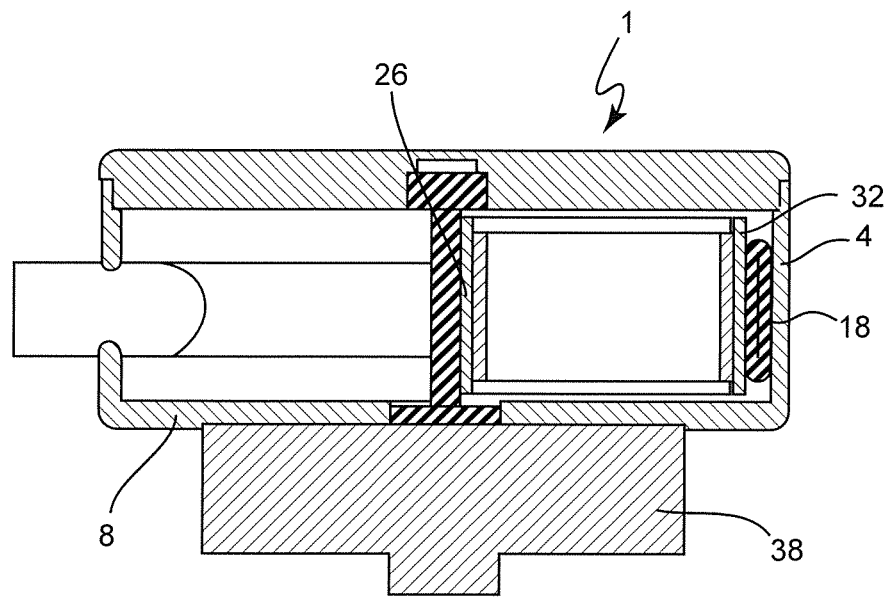
FIG. 9 shows a schematic sectional view through a peristaltic pump.

FIG. 9 shows a schematic sectional view through a peristaltic pump 1 as shown in FIGS. 5, 6, 7 and 8. Here too, the shaft 26, the roller 32 and the hose 18 form a frictional planetary gear, such that the roller 32 does not have a roller axle 22. The necessary torque is transferred solely by the frictional contact between the roller 32 and the shaft 26. The hose 18 is squeezed shut between the roller 32 and the circumferential wall 4 of the housing 2 of the peristaltic pump 1. A motor 38 is shown under the floor 8 of the housing 2, which motor 38 is designed, for example, as a disk rotor motor and drives the shaft 26.

Figure 10:
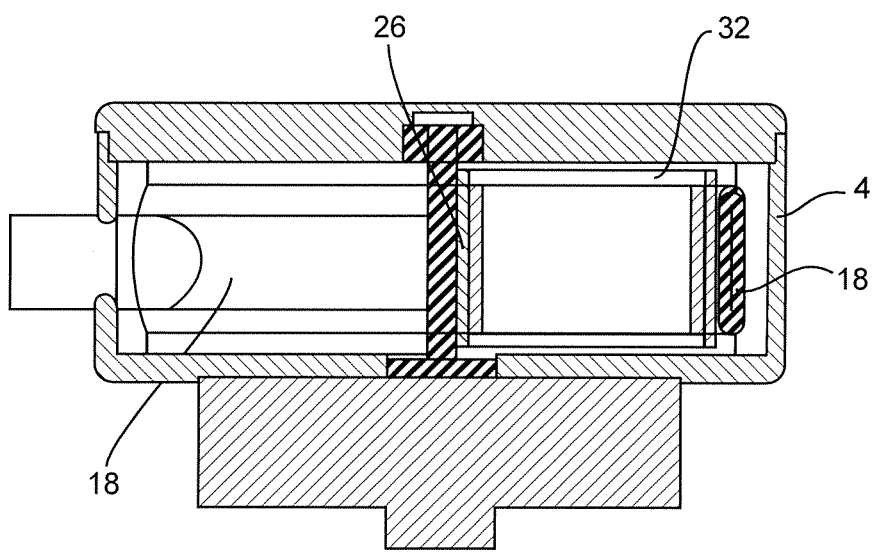
FIG. 10 shows another sectional view through a peristaltic pump for a prosthesis according to an illustrative embodiment of the present invention.

The same view is shown in FIG. 10, with the difference that on the inside face of the circumferential wall 4 there is a guide 28 which prevents shifting and slipping of the hose 18 in the axial direction with respect to the shaft 26, i.e. upward or downward in FIG. 10. However, the guide 28, which can be designed in the form of a silicone pad for example, not only serves to guide the hose but also as tolerance compensation. For example, the elasticity of the guide 28 can compensate for manufacturing tolerances or different expansions of the component parts during temperature changes. Even if the hose 18 loses some diameter, for example as a result of wear, this can be compensated by the guide 28. The same applies in the event of a decreasing elasticity of the hose 18 in the course of permanent operation.

Figure 11:
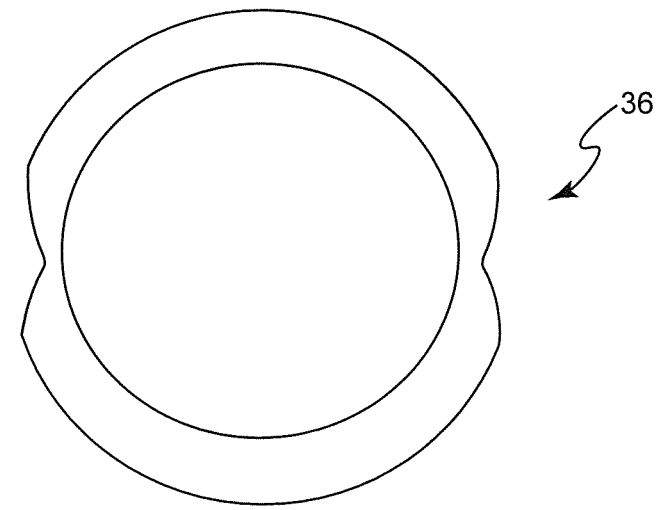
FIG. 11 shows the schematic view of two preferred hose cross sections.
Figure 11:
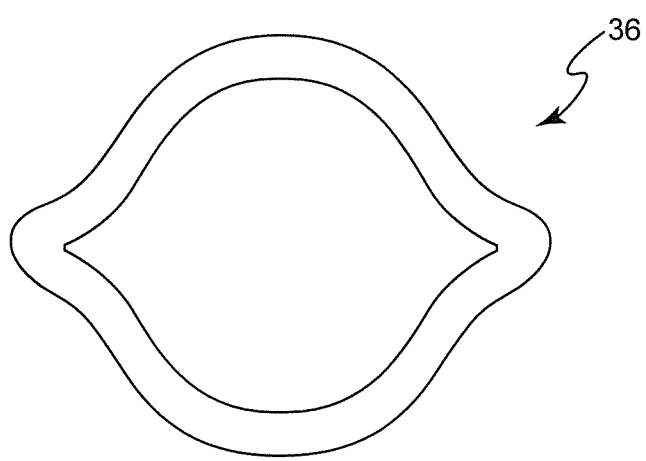

FIG. 11 shows the schematic view of two hose cross sections 36. When the hose 18 is squeezed together between the roller 32 and the inside face of the circumferential wall 4 of the housing 2 of the peristaltic pump 1, a high mechanical load occurs particularly in the edge area of the cross section, on account of the strong deformation in this area. Therefore, the highest degree of wear of the hoses 18 can also be expected to occur in this area in this type of pump. To prevent this, and to ensure the functioning of the peristaltic pump 1 over a long period of time, certain hose cross sections 36 can be chosen, of which two particularly preferred embodiments are shown as examples in FIG. 11. In the upper part of FIG. 11, the hose 18 has a circular hose cross section, with the wall thickness being reduced on the right edge and on the left edge. A hose with a cross section of this kind is arranged in the peristaltic pump 1 in such a way that, when it is squeezed together, the pressure acts from the top downward in the orientation shown in FIG. 11. The narrowed parts in the wall thickness are thus situated precisely at those locations where the greatest mechanical load occurs. Since there is less material present here that has to be squeezed and deformed, the mechanical loads are less strong, such that wear is greatly reduced.

In the lower part of FIG. 11, another cross section is shown that likewise leads to less mechanical loading, particularly at the edges of the hose 18 when the latter is squeezed together. In this embodiment too, the hose 18 is to be arranged in the housing 2 of the peristaltic pump 1 in such a way that the pressure acts from the top downward, in the orientation shown in FIG. 11, and consequently squeezes the hose together in this direction. It will be readily appreciated that, with the cross section shown in the lower part of FIG. 11, the hose is particularly easy to press together in this direction and squeeze shut, such that the particular cross-sectional shape means once again that there is much less pronounced mechanical loading in the right-hand and left-hand edge areas. Therefore, with this cross section too, the lifetime of the hose, and therefore the functionality of the peristaltic pump 1, is greatly prolonged.

The chosen shape of the cross section 36 provides structural strength since, after being pressed shut by the pump element 20, the hose 18 once again assumes its original shape. In addition, the degree of wear is reduced at the locations that are particularly subject to loading when the hose is pressed shut.

Figure 12:
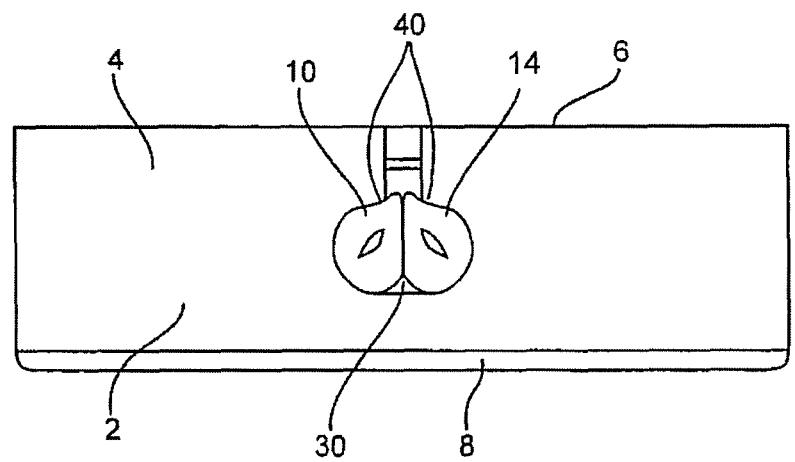
FIG. 12 shows the schematic side view of a peristaltic pump according to an illustrative embodiment of the present invention.

FIG. 12 shows a schematic side view of the peristaltic pump according to an illustrative embodiment of the present invention. The housing 2 has the lid 6, the floor 8 and the circumferential wall 4. In the circumferential wall 4 is the opening 30 through which the first hose end 10 and the second hose end 14 are guided.

It will be seen in FIG. 12 that the opening 30 is oval and has a web 40 in the upper area. It will be seen that the first hose end 10 and the second hose end 14 form a slight bead in this area. The first hose end 10 and the second hose end 14 are pressed through the web 40 into the position shown in FIG. 12, such that both hose ends 10, 14 are opened slightly, with the result that a medium, for example air, can be pumped through the hose. When choosing the shape of the opening 30, care must therefore be taken to ensure that the first hose end 10 and the second hose end 14 are not completely squeezed shut, so that a medium can be pumped through the hose 18. At the same time, however, the opening 30 chosen must be small enough to ensure that the first hose end 10 and the second hose end 14 are arranged so close to each other that a pump element 20, for example the roller 32, rotating inside the housing 2 of the peristaltic pump 1 can press both hose ends 10, 14 shut simultaneously in order to avoid a return flow of the medium.

Both criteria are satisfied by the shape of the opening 30 shown in FIG. 12. If the opening 30 were smaller, the first hose end 10 and the second hose end 14 would be completely pressed shut by the opening 30 alone, such that a medium could no longer be conveyed through them. If the opening 30 were larger, a pump element 20 rotating inside the pump 1 could no longer press both hose ends 10, 14 shut simultaneously.

Figure 13:
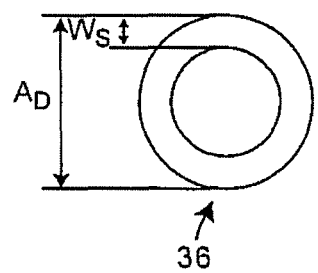
FIG. 13 shows a schematic view of a hose cross section.

FIG. 13 shows a view of the schematic hose cross section 36. The external diameter of the hose is designated by $A_D$, while $W_S$ indicates the wall thickness of the hose. The wall thickness $W_S$ of the hose 18 is advantageously between 0.5 and 1.5 mm.

Figure 14:
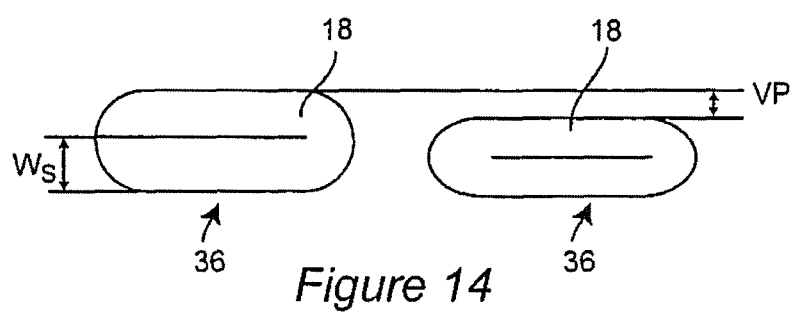
FIG. 14 shows a schematic view of a hose laid together and of a hose pressed together.

FIG. 14 shows the hose cross section 36. In the left-hand part of FIG. 14, the hose cross section 36 is pressed together such that an upper wall and a lower wall of the hose 18 rest on each other, with the result that no fluid can any longer be conveyed through the hose 18. The overall height of the hose 18 thus laid together corresponds to twice the wall thickness $W_S$. Additional squeezing of the hose material does not take place in this example. By contrast, in the right-hand part of FIG. 14, the hose 18 is shown in the state to which it is brought by a rotating pump element 20. It will be seen that the hose 18 is pressed together more than would actually be necessary to close the hose cross section 36. The difference between the only slightly closed hose 18 shown in the left-hand part and the hose pressed together in the right-hand part of FIG. 14 is characterized by VP and designates the pressing of the hose. In a preferred embodiment, this is between 20 and 25%. In the illustrative embodiment shown in FIG. 14, the pressing VP thus corresponds to 20% to 25% of twice the wall thickness $W_S$.

Figure 15:
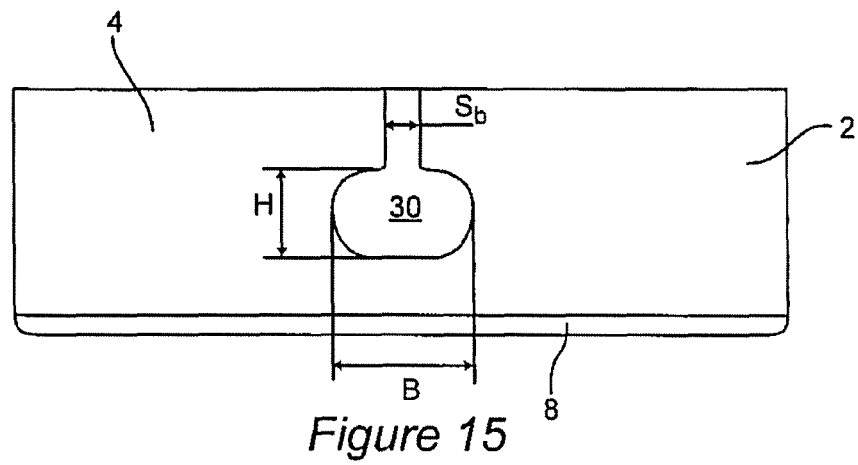
FIG. 15 shows a schematic side view of a pump housing.

FIG. 15 shows a side view of the housing 2 very similar to the view shown in FIG. 12. This view shows the circumferential wall 4 and floor 8 of the housing 2. In the circumferential wall 4, the opening 30 is shown through which the hose 18 (not shown in FIG. 15) is guided into and out of the housing 2.

The dimensions described here for the hose 28 used and the corresponding measurements of the housing 2 and of the other components of the peristaltic pump 1 are adapted to an embodiment in which the hose 18 is a TPE hose. They simply represent particularly preferred embodiments and dimensions of the individual components.

FIG. 15 shows dimensions of the opening 30 and of the web 40. The height of the opening 30 is indicated by H. The height H is preferably slightly smaller than the external diameter $A_D$ of the hose. The following preferably applies: $H=A_D/1.25$.

The width of the opening 30 is designated by B. Since the hose 18 has to be guided twice through the opening 30, the width B is preferably larger than the external diameter $A_D$ but smaller than twice the external diameter $A_D$. The following preferably applies for the width B: $B=A_D/0.8\overline{3}$.

The width of the web 40 is characterized by $S_b$. For this, the following preferably applies: $S_b=VP*2*W_S$.

Figure 16:
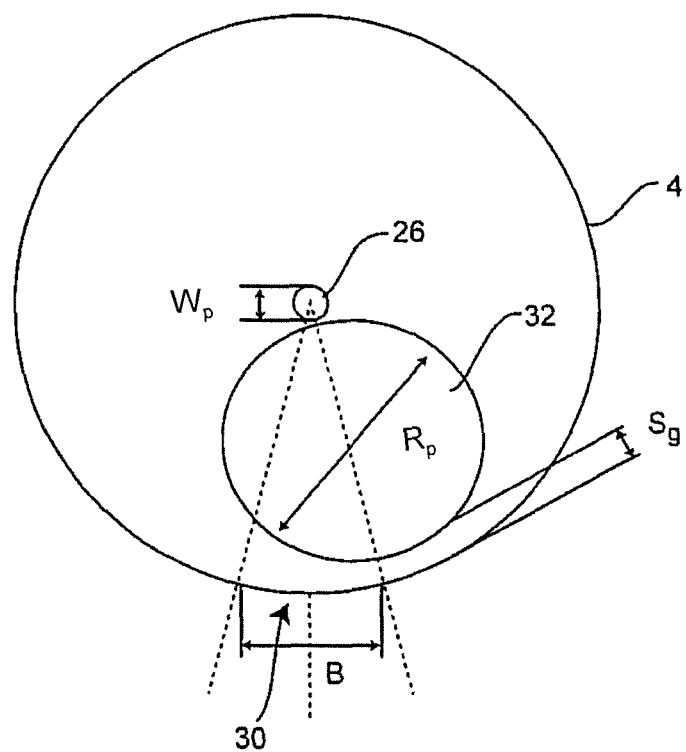
FIG. 16 shows a schematic plan view of a pump housing with the lid removed.

FIG. 16 shows a schematic plan view of the pump housing 2, from which the lid 6 has been removed. The view shows the circumferential wall 4 surrounding the shaft 26 arranged at the center. The roller 32 extends between this shaft 26 and the hose 18 (not shown in FIG. 16) extending on the circumferential wall 4. The width B of the opening 30 is also shown in FIG. 16. The roller 32 has a roller diameter $R_D$, while the shaft 26 has a shaft diameter $W_D$. This gives the step-down ratio $W_D/R_D$ for the driven shaft 26.

With a given roller diameter $R_D$, a given external diameter $A_D$ of the hose and a given internal diameter of the circumferential wall 4, the radius of the shaft is given by the following relationship: shaft radius $W_R$=housing internal diameter minus thickness of the compressed hose minus roller diameter $R_D$. The diameter of the compressed hose is equal to twice the wall thickness $W_S$ multiplied by 1 minus the pressing VP.

A central condition for the size of the opening 30 that is to be chosen is the ratio of the roller diameter $R_D$ to the width B of the opening 30. In a preferred embodiment, the ratio of roller diameter $R_D$ to the width B of the opening 30 is 2.34, such that the roller diameter $R_D$ corresponds to 2.34 times the width B of the opening 30.

Of course, functioning peristaltic pumps 1 for prostheses according to an illustrative embodiment of the present invention are also conceivable with other dimensions, measurements and materials.

Figure 17:
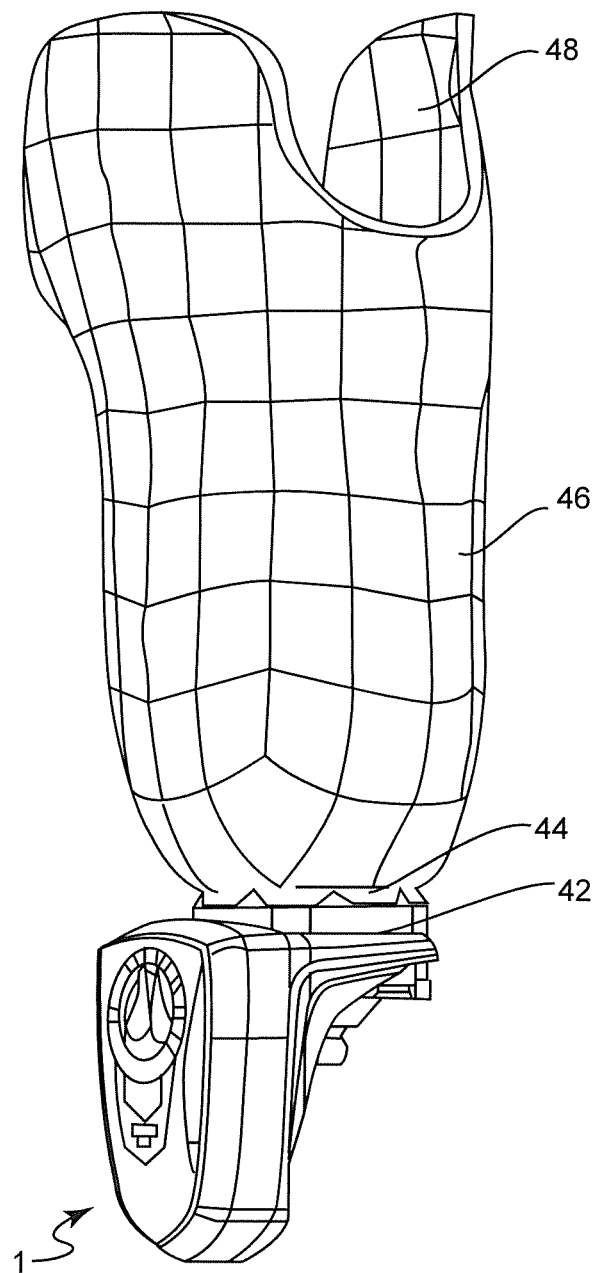
FIG. 17 shows a schematic 3D view of a prosthesis socket with a pump mounted thereon.
Figure 18:
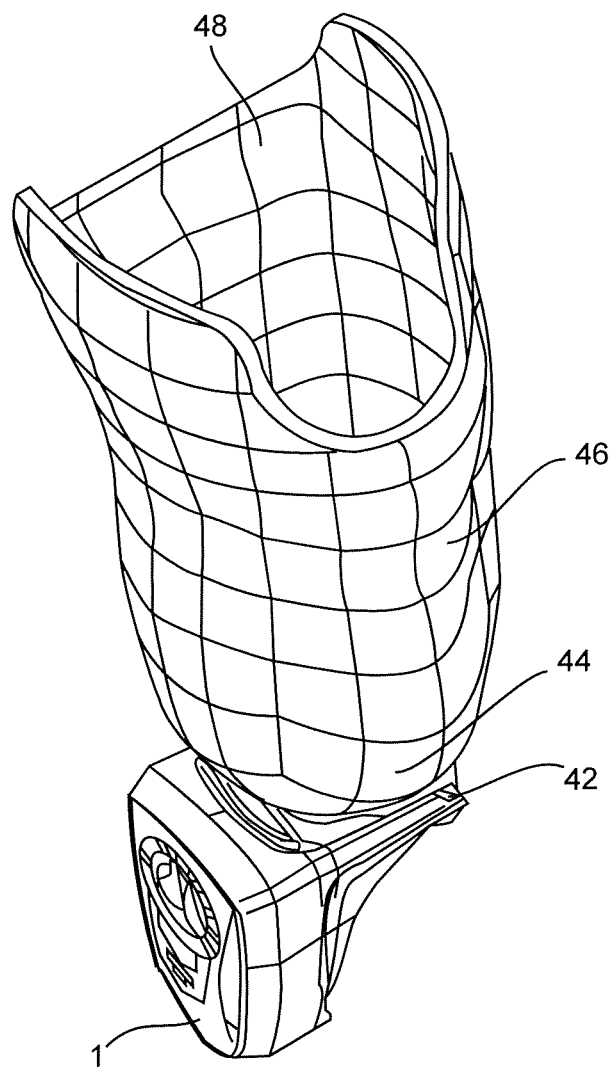
FIG. 18 shows the view from FIG. 17 at another angle.

FIG. 17 shows a schematic 3D view of a peristaltic pump 1 arranged on a pump holder 42, which is arranged on a distal end 44 of a prosthesis socket 46. It will be seen in the upper area that the prosthesis socket 46 has an inner face 48, via which the socket 46 bears on an amputation stump (not shown). FIG. 18 shows the view from FIG. 17 at a slightly different angle.

Figure 19:
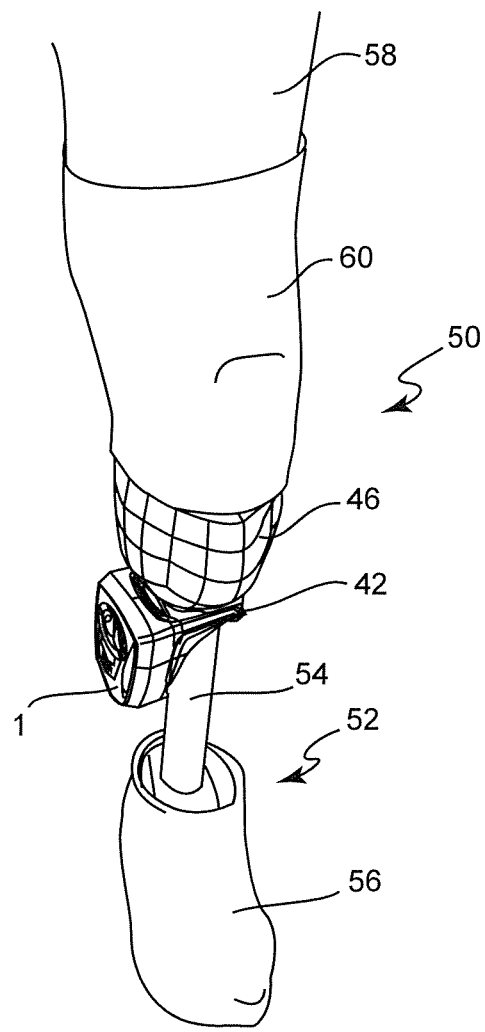
FIG. 19 shows a schematic view of a prosthesis according to an illustrative embodiment of the present invention arranged on an amputation stump.
Figure 20:
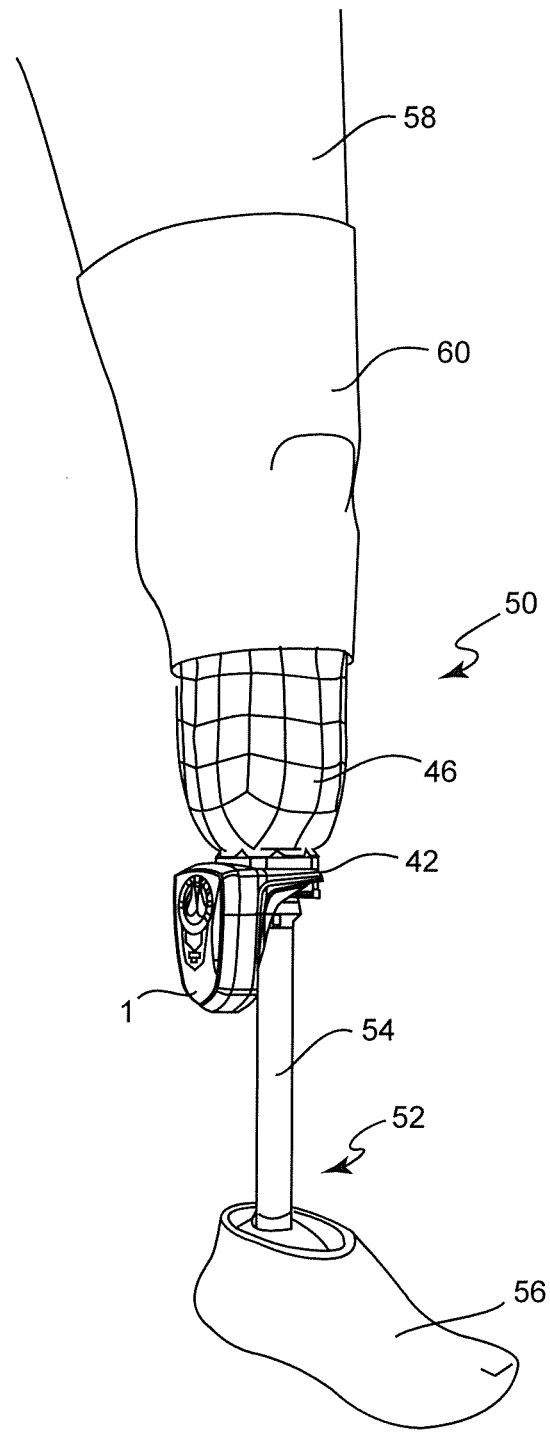
FIG. 20 shows the view from FIG. 19 at another angle.

FIGS. 19 and 20 show a prosthesis 50 according to an illustrative embodiment of the present invention from two slightly different angles. The peristaltic pump 1 can be seen arranged on the prosthesis socket 46 via the pump holder 42. At the distal end there is a prosthesis device 52, which has a tube element 54 and, arranged at the distal end of the latter, a foot element 56. At the upper edge of each of FIGS. 19 and 20, an amputation stump 58 can be seen which is arranged in the prosthesis socket 46. A so-called knee cap 60 or a sleeve is pulled over the connection site between prosthesis socket 46 and amputation stump 58. This knee cap 60 ensures an airtight closure of the volume enclosed between the prosthesis socket 46 and the amputation stump 58. It is of course also conceivable, for example, to arrange a sealing element on the inner face 48 of the prosthesis socket 46 in order to provide an airtight closure of the volume located between the prosthesis socket 46 and the amputation stump 58. Alternatively or in addition to this, a liner can also be provided, which is pulled over the amputation stump 58 before the latter is inserted into the prosthesis socket 46.

LIST OF REFERENCE SIGNS 1 peristaltic pump
2 housing
4 circumferential wall
6 lid
8 floor
10 first hose end
12 first opening
14 second hose end
16 second opening
18 hose
20 pump element
22 roller axle
24 drive disk
26 shaft
28 guide
30 opening
32 roller
34 roughened area
36 hose cross section
38 motor
40 web
42 pump holder
44 distal end
46 prosthesis socket
48 inner face
50 prosthesis
52 prosthesis device
54 tube element
56 foot element
58 amputation stump
60 knee cap
$A_D$ external diameter of the hose
$W_S$ wall thickness
VP pressing
H height
B width
$S_b$ web width
$R_D$ roller diameter
$W_D$ shaft diameter
$W_R$ shaft radius

The invention claimed is:

1. Prosthesis, comprising:
   a prosthesis socket which has an inner face and which is designed to be arranged on an amputation stump, such that the inner face is directed toward the amputation stump and a volume of air or gas is enclosed between the inner face and the amputation stump, and
   a pump for generating a vacuum in the volume when the prosthesis socket is arranged on the amputation stump, wherein the pump is a peristaltic pump with a hose and a pump element, wherein the peristaltic pump is configured to assure opening up of said hose after squeezing of said hose by said pump element after generating said vacuum in the volume.

2. Prosthesis according to claim 1 wherein the pump element includes exactly one pump element, and wherein the peristaltic pump comprises a housing which has a circumferential wall, a floor and a lid and in which said exactly one pump element is arranged.

3. Prosthesis according to claim 2, wherein an opening through which the hose is guided into the housing and out of the housing is provided in the circumferential wall.

4. Prosthesis according to claim 3, wherein the hose is guided in the housing in such a way that at no point does the hose overlap itself.

5. Prosthesis according to claim 3, wherein the hose is made of silicone or of a thermoplastic elastomer or of polyurethane.

6. Prosthesis according to claim 2, wherein the pump element is a roller, which is arranged in the housing such that it can rotate about a shaft and pinches the hose shut.

7. Prosthesis according to claim 6, wherein the hose is guided along an inner side of the circumferential wall and forms a frictional planetary gear with the roller and the shaft.

8. Prosthesis according to claim 6, wherein the roller is a hollow roller.

9. Prosthesis according to claim 2, wherein a friction-reducing layer is arranged on an inner side of the lid and/or on an inner side of the floor of the housing.

10. Prosthesis according to claim 9 wherein said friction-reducing layer is a polytetrafluoroethane (PTFE) fabric sheet.

11. Prosthesis according to claim 2 further comprising means for applying said vacuum inside said housing.

12. Prosthesis according to claim 1, further comprising a motor for driving the pump, which motor is designed in the form of a disk rotor motor.

13. Prosthesis according to claim 1 wherein said hose has an external diameter of 5 mm and a wall thickness of 1 mm, and a shore hardness of 60-65.

14. Prosthesis according to claim 1 wherein said hose is made from a thermoplastic material.

15. Prosthesis according to claim 1 wherein said hose is coated on its inner walls to prevent adherence of the inner walls to each other.

16. Prosthesis according to claim 1 wherein said hose has a cross-sectional shape which prevents or reduces bead formation.

* * * * *